US012780790B2

(12) United States Patent
Seo et al.

(10) Patent No.: US 12,780,790 B2
(45) Date of Patent: Nov. 3, 2026

(54) METHOD FOR PRODUCING TETRAHYDROFURAN, GAMMA-BUTYROLACTONE, OR 1,4-BUTANEDIOL

(71) Applicant: CJ CHEILJEDANG CORPORATION, Seoul (KR)

(72) Inventors: Jang-Woo Seo, Seoul (KR); Jinwoo Jeon, Seoul (KR); Youngsu You, Seoul (KR); Joo Young Lee, Seoul (KR); Jieun Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 476 days.

(21) Appl. No.: 18/573,415

(22) PCT Filed: Jun. 24, 2022

(86) PCT No.: PCT/KR2022/009050

§ 371 (c)(1),
(2) Date: Dec. 21, 2023

(87) PCT Pub. No.: WO2022/270982

PCT Pub. Date: Dec. 29, 2022

(65) Prior Publication Data

US 2024/0287011 A1 Aug. 29, 2024

(30) Foreign Application Priority Data

Jun. 25, 2021 (KR) ........................ 10-2021-0083443
Mar. 21, 2022 (KR) ........................ 10-2022-0034844

(51) Int. Cl.

| | |
|---|---|
| ***C07D 307/08*** | (2006.01) |
| ***C07C 29/149*** | (2006.01) |
| ***C07D 307/33*** | (2006.01) |
| ***C08J 11/16*** | (2006.01) |

(52) U.S. Cl.

CPC .......... *C07D 307/08* (2013.01); *C07C 29/149* (2013.01); *C07D 307/33* (2013.01); *C08J 11/16* (2013.01); *C08J 2367/00* (2013.01)

(58) Field of Classification Search

CPC ....... C07C 29/149; C07C 29/76; C07C 31/20; C07D 307/08; C07D 307/33; C08J 11/16; C08J 2367/00

See application file for complete search history.

(56) References Cited

U.S. PATENT DOCUMENTS

| | | | |
|---|---|---|---|
| 2001/0029302 | A1 | 10/2001 | Cho et al. |
| 2005/0182235 | A1 | 8/2005 | Zhong et al. |
| 2007/0026007 | A1 | 2/2007 | Poznansky et al. |
| 2015/0037615 | A1 | 2/2015 | Xiao et al. |
| 2015/0376152 | A1 | 12/2015 | Samuelson et al. |
| 2018/0002303 | A1 | 1/2018 | Duefert et al. |

FOREIGN PATENT DOCUMENTS

| | | | |
|---|---|---|---|
| JP | 09-012492 | A | 1/1997 |
| KR | 10-2001-0095500 | A | 11/2001 |
| KR | 10-0530781 | B1 | 11/2005 |
| KR | 10-2010-0132624 | A | 12/2010 |
| WO | 99-25678 | A1 | 5/1999 |
| WO | 03/051813 | A1 | 6/2003 |

OTHER PUBLICATIONS

International Search Report issued in corresponding International Patent Application No. PCT/KR2022/009050 dated Sep. 29, 2022.
Office Action issued in corresponding Japanese Patent Application No. 2023-577260, dated Nov. 19, 2024.
Extended European Search Report issued in corresponding European Patent Application No. 22828829.6, dated May 6, 2025.

*Primary Examiner* — Jafar F Parsa
(74) *Attorney, Agent, or Firm* — Morgan, Lewis & Bockius LLP

(57) ABSTRACT

The present invention relates to a method for producing tetrahydrofuran, gamma-butyrolactone, or 1,4-butanediol. Particularly, according to an embodiment of the present invention, by using polyhydroxyalkanoate (PHA), the yield of tetrahydrofuran, gamma-butyrolactone, or 1,4-butanediol which is environmentally friendly due to excellent biodegradability and biocompatibility can be effectively controlled without complicated additional processes.

18 Claims, 1 Drawing Sheet

[Fig. 1]
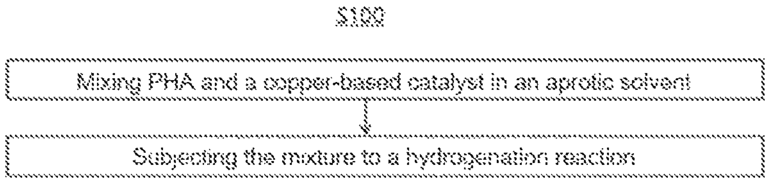
[Fig. 2]
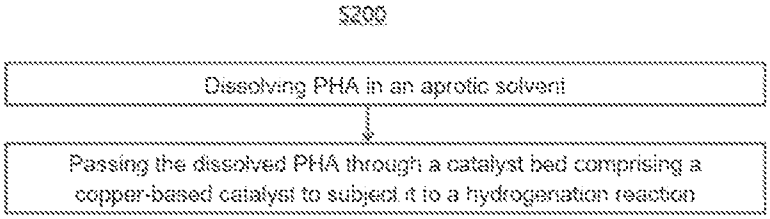

METHOD FOR PRODUCING TETRAHYDROFURAN, GAMMA-BUTYROLACTONE, OR 1,4-BUTANEDIOL

TECHNICAL FIELD

The present invention relates to a process for preparing tetrahydrofuran, gamma-butyrolactone, or 1,4-butanediol using a polyhydroxyalkanoate (PHA).

BACKGROUND ART

Tetrahydrofuran is a solvent widely used in the field of organic chemistry. It is widely used in the production of natural and synthetic resins on an industrial scale; thus, its demand is high. In addition, gamma-butyrolactone is a solvent widely used as a starting material in various synthesis methods. For example, it plays an important role in the production of substances such as N-methylpyrrolidone, butyric acid, and its derivatives. It is also known as an important solvent in the production of acrylates, styrene polymers, polymers, and synthetic resins.

Conventionally, a method for preparing tetrahydrofuran or gamma-butyrolactone using succinic acid, maleic acid, or an anhydride thereof has been used. However, it is difficult to control side reactions, and the yield of the target material is low. In addition, a method of producing tetrahydrofuran or gamma-butyrolactone using butanediol has been used, but the price of butanediol is relatively high, and the manufacturing process is complicated. Thus, research on a manufacturing method capable of controlling the yield of a desired material and having excellent process efficiency is ongoing.

Meanwhile, polyhydroxyalkanoates (PHA) are biodegradable polymers composed of several types of hydroxyl carboxylic acids produced by numerous microorganisms and used as intracellular storage materials. Polyhydroxyalkanoates have physical properties similar to those of conventional petroleum-derived synthetic polymers such as polybutylene adipate terephthalate (PBAT), polybutylene succinate (PBS), polybutylene succinate terephthalate (PBST), and polybutylene succinate adipate (PBSA), exhibit complete biodegradability, and are excellent in biocompatibility.

PRIOR ART DOCUMENT

Patent Document (Patent Document 1) Korean Laid-open Patent Publication No. 2001-0095500

DISCLOSURE OF INVENTION

Technical Problem

Accordingly, the present invention aims to provide a process for preparing tetrahydrofuran, gamma-butyrolactone, or 1,4-butanediol, which uses a polyhydroxyalkanoate (PHA), whereby it is environmentally friendly by virtue of its excellent biodegradability and biocompatibility, and can effectively control the yield of tetrahydrofuran, gamma-butyrolactone, or 1,4-butanediol without complicated additional processes.

Solution to Problem

The process for preparing tetrahydrofuran, gamma-butyrolactone, or 1,4-butanediol according to an embodiment of the present invention comprises subjecting a polyhydroxyalkanoate (PHA) to a hydrogenation reaction using a copper-based catalyst in an aprotic solvent.

According to another embodiment of the present invention, the hydrogenation reaction may be carried out at a temperature of 50° C. to 500° C. and a pressure of 1 bar to 100 bar.

The process for preparing tetrahydrofuran, gamma-butyrolactone, or 1,4-butanediol according to an embodiment of the present invention may comprise mixing a polyhydroxyalkanoate (PHA) and a copper-based catalyst with an aprotic solvent; and subjecting the mixture to a hydrogenation reaction.

According to another embodiment of the present invention, prior to the hydrogenation reaction step, it comprises removing oxygen in the reactor; and adjusting the internal pressure of the reactor to 1 bar to 100 bar by injecting hydrogen gas.

According to another embodiment of the present invention, the weight ratio of the polyhydroxyalkanoate (PHA) to the copper-based catalyst may be 1:0.01 to 5.

According to another embodiment of the present invention, the hydrogenation reaction may be carried out at a stirring speed of 200 rpm to 2,000 rpm for 1 hour to 10 hours.

The process for preparing tetrahydrofuran, gamma-butyrolactone, or 1,4-butanediol according to an embodiment of the present invention may comprise dissolving a polyhydroxyalkanoate (PHA) in an aprotic solvent; and passing the dissolved polyhydroxyalkanoate (PHA) through a catalyst bed comprising a copper-based catalyst to subject it to a hydrogenation reaction.

According to another embodiment of the present invention, hydrogen gas is injected in the hydrogenation reaction step, and the hydrogen gas may be injected in a mole number of 1 time to 500 times the number of moles of the polyhydroxyalkanoate (PHA) monomer.

According to another embodiment of the present invention, the weight hourly space velocity (WHSV) of the copper-based catalyst relative to the polyhydroxyalkanoate (PHA) may be $0.1\ h^{-1}$ to $10\ h^{-1}$.

According to another embodiment of the present invention, the copper-based catalyst is supported on a support, and the support may comprise at least one selected from the group consisting of carbon, zeolite, $Al_2O_3$, $SiO_2$, $TiO_2$, $ZrO_2$, MgO, and $Cr_2O_3$.

According to another embodiment of the present invention, the copper-based catalyst is a copper catalyst or a copper-metal composite catalyst, and the copper-metal composite catalyst may comprise copper-metal complex which comprises at least one metal selected from the group consisting of Mn, Zn, Mg Co, Ni, Cr, and Fe, other than copper.

According to another embodiment of the present invention, the support may be $Al_2O_3$, $SiO_2$, $TiO_2$, or $ZrO_2$, and the copper-based catalyst may be a Cu catalyst, a Cu—Mn catalyst, a Cu—Zn catalyst, or a Cu—Mg catalyst.

According to another embodiment of the present invention, the content of copper or copper-metal complex in the copper-based catalyst supported on the support may be 0.1% by weight to 85% by weight based on the total weight of the support.

According to another embodiment of the present invention, the aprotic solvent may comprise at least one selected from the group consisting of acetone, dioxane, methyl acetate, ethyl acetate, N,N-dimethylformamide, N,N-dimethylacetamide, N-methylpyrrolidone, acetonitrile, propionitrile, butyronitrile, benzonitrile, acrylonitrile, dimethylsulfoxide, dichloromethane, dimethylpropylene urea, and hexamethylphosphate triamide.

According to another embodiment of the present invention, the yield of tetrahydrofuran, gamma-butyrolactone, or 1,4-butanediol may exceed 65% by mole.

According to another embodiment of the present invention, prior to the hydrogenation reaction, it may further comprise pretreating the polyhydroxyalkanoate the (PHA), wherein the pretreatment step may comprise purifying polyhydroxyalkanoate (PHA) using a solvent extraction method.

According to another embodiment of the present invention, after the hydrogenation reaction, it may further comprise treating the reaction product with one or more steps selected from the group consisting of a distillation step, an ion exchange step, a solvent extraction step, and an adsorption step.

According to an embodiment of the present invention, the polyhydroxyalkanoate (PHA) may comprise a 4-hydroxybutyrate (4-HB) repeat unit in an amount of 0.1% by weight to 100% by weight.

According to an embodiment of the present invention, the polyhydroxyalkanoate (PHA) may have an average particle size of 0.5 μm and 5 μm.

According to an embodiment of the present invention, the polyhydroxyalkanoate (PHA) may have a polydispersity index (PDI) of less than 2.5.

Advantageous Effects of Invention

In the process for preparing tetrahydrofuran, gamma-butyrolactone, or 1,4-butanediol according to an embodiment of the present invention, a polyhydroxyalkanoate (PHA) is used to produce tetrahydrofuran, gamma-butyrolactone, or 1,4-butanediol through a hydrogenation reaction; thus, it is environmentally friendly by virtue of its excellent biodegradability and biocompatibility. It is also possible to effectively control the yield of tetrahydrofuran, gamma-butyrolactone, or 1,4-butanediol without complicated additional processes.

BRIEF DESCRIPTION OF DRAWINGS

FIG. 1 shows a schematic flow chart (S100) of the process for preparing tetrahydrofuran, gamma-butyrolactone, or 1,4-butanediol according to an embodiment of the present invention.

FIG. 2 shows a schematic flow chart (S200) of the process for preparing tetrahydrofuran, gamma-butyrolactone, or 1,4-butanediol according to another embodiment of the present invention.

BEST MODE FOR CARRYING OUT THE INVENTION

Hereinafter, the present invention will be described in detail. The present invention is not limited to the disclosures given below, but it may be modified into various forms as long as the gist of the invention is not changed.

Throughout the present specification, when a part is referred to as "comprising" an element, it is understood that other elements may be comprised, rather than other elements are excluded, unless specifically stated otherwise.

All numbers and expressions related to the quantities of components, reaction conditions, and the like used herein are to be understood as being modified by the term "about," unless otherwise indicated.

In the present specification, in the case where an element is mentioned to be formed "on" or "under" another element, it means not only that one element is directly formed "on" or "under" another element, but also that one element is indirectly formed on or under another element with other element(s) interposed between them.

The process for preparing tetrahydrofuran, gamma-butyrolactone, or 1,4-butanediol according to an embodiment of the present invention comprises subjecting a polyhydroxyalkanoate (PHA) to a hydrogenation reaction using a copper-based catalyst in an aprotic solvent.

It has been difficult to selectively control the yield of a desired material in the methods for producing tetrahydrofuran, gamma-butyrolactone, or 1,4-butanediol conventionally used. Specifically, when tetrahydrofuran, gamma-butyrolactone, or 1,4-butanediol is prepared using succinic acid, maleic acid, or an anhydride thereof, the yield of tetrahydrofuran can be increased whereas there is a problem in that a complicated additional process has to be carried out in order to increase the yield of gamma-butyrolactone or 1,4-butanediol. Specifically, a process for converting succinic acid or maleic acid to an anhydride is additionally required, or a process such as an esterification reaction is additionally required, which increases process time and cost, resulting in low process efficiency.

For example, when succinic acid is used as a raw material, biomass is removed to obtain succinic anhydride from the fermentation broth, the pH is acidified to 3 by applying hydrochloric acid or the like, and a high-temperature, reduced-pressure (180° C., 200 mbar) distillation process is additionally performed to obtain succinic anhydride. In addition, when maleic acid is used as a raw material, specifically, when diethyl maleate produced through the esterification reaction of ethanol is used as a raw material, the acid and by-products formed during the esterification reaction may reduce the lifespan of the catalyst, and ethanol can be produced again after the hydrogenation reaction, thereby leading to a problem in that an ethanol separation and recovery process is additionally required.

In the process for preparing tetrahydrofuran, gamma-butyrolactone, or 1,4-butanediol according to an embodiment of the present invention, however, a polyhydroxyalkanoate (PHA) is used; thus, it is environmentally friendly by virtue of its excellent biodegradability and biocompatibility. It is also possible to effectively control the yield of tetrahydrofuran, gamma-butyrolactone, or 1,4-butanediol without complicated additional processes, whereby the process can be simplified, and the process efficiency is excellent.

First, the process for preparing tetrahydrofuran, gamma-butyrolactone, or 1,4-butanediol according to an embodiment of the present invention is carried out using a polyhydroxyalkanoate (PHA).

PHA is a natural thermoplastic polyester polymer that accumulates in microbial cells. Since it is a biodegradable material, it can be composted and finally decomposed into carbon dioxide, water, and organic waste without generating toxic waste.

Specifically, PHA is a natural thermoplastic polyester polymer that accumulates in microbial cells. It is formed by accumulating PHA in cells to store carbon and energy when certain bacteria are supplied with nutrients (nitrogen source, phosphorus, and the like) disproportionately.

In addition, PHA has physical properties similar to those of conventional petroleum-derived synthetic polymers such as polybutylene adipate terephthalate (PBAT), polybutylene succinate (PBS), polybutylene succinate terephthalate (PBST), and polybutylene succinate adipate (PBSA), exhibit complete biodegradability, and are excellent in biocompatibility.

In particular, unlike other environmentally friendly plastic materials such as PBS, PLA, and PTT, PHA can be synthesized from more than 150 types of monomers, so that hundreds of types of PHA can be prepared depending on the types of monomers. Hundreds of different types of PHA depending on the types of monomers have completely different structures and properties.

The PHA may be composed of a single monomer repeat unit in living cells and may be formed by polymerizing one or more monomer repeat units. Specifically, the PHA may be a homo-polyhydroxyalkanoate (hereinafter, referred to as HOMO PHA) or a copolymerized polyhydroxyalkanoate (hereinafter, referred to as a copolymerized PHA), that is, a copolymer in which different repeat units are randomly distributed in the polymer chain.

Examples of repeat units that may be contained in the PHA include 2-hydroxybutyrate, lactic acid, glycolic acid, 3-hydroxybutyrate (hereinafter, referred to as 3-HB), 3-hydroxypropionate (hereinafter, referred to as 3-HP), 3-hydroxyvalerate (hereinafter, referred to as 3-HV), 3-hydroxyhexanoate (hereinafter, referred to as 3-HH), 3-hydroxyheptanoate (hereinafter, referred to as 3-HHep), 3-hydroxyoctanoate (hereinafter, referred to as 3-HO), 3-hydroxynonanoate (hereinafter, referred to as 3-HN), 3-hydroxydecanoate (hereinafter, referred to as 3-HD), 3-hydroxydodecanoate (hereinafter, referred to as 3-HDd), 4-hydroxybutyrate (hereinafter, referred to as 4-HB), 4-hydroxyvalerate (hereinafter, referred to as 4-HV), 5-hydroxyvalerate (hereinafter, referred to as 5-HV), and 6-hydroxyhexanoate (hereinafter, referred to as 6-HH). The PHA may contain one or more repeat units selected from the above.

Specifically, the PHA may comprise one or more repeat units selected from the group consisting of 3-HB, 4-HB, 3-HP, 3-HH, 3-HV, 4-HV, 5-HV, and 6-HH.

More specifically, the PHA may comprise a 4-HB repeat unit in an amount of 0.1% by weight to 100% by weight. For example, the PHA may comprise a 4-HB repeat unit in an amount of 0.2 to 100% by weight, 0.5 to 100% by weight, 1 to 100% by weight, 5% by weight to 100% by weight, 10% by weight to 100% by weight, 20% by weight to 100% by weight, 30% by weight to 100% by weight, 40% by weight to 100% by weight, 50% by weight to 100% by weight, 60% by weight to 100% by weight, 70% by weight to 100% by weight, 80% by weight to 100% by weight, or 90% by weight to 100% by weight. That is, the PHA may be a HOMO PHA composed of a 4-HB repeat unit alone or a copolymerized PHA comprising a 4-HB repeat unit.

For example, the PHA may be a copolymerized PHA that comprises a 4-HB repeat unit and further comprises one repeat unit different from the 4-HB repeat unit, or two, three, four, five, six, or more repeat units different from each other. For example, the PHA may be poly-3-hydroxybutyrate-co-4-hydroxybutyrate (hereinafter, referred to as 3HB-co-4HB).

In addition, the PHA may comprise isomers. For example, the PHA may comprise structural isomers, enantiomers, or geometric isomers. Specifically, the PHA may comprise structural isomers.

The PHA may preferably be a HOMO PHA composed of 4-HB repeat units alone from the viewpoint of maximizing the effect of yield control of tetrahydrofuran, gamma-butyrolactone, or 1,4-butanediol.

In addition, the PHA may be a copolymerized PHA with controlled crystallinity. For example, the PHA may comprise at least one or more of a 4-HB repeat unit, and the content of the 4-HB repeat unit may be controlled to adjust the crystallinity of the PHA.

For example, the PHA may be a copolymerized polyhydroxyalkanoate (PHA) that comprises at least one repeat unit selected from the group consisting of 3-hydroxybutyrate (3-HB), 4-hydroxybutyrate (4-HB), 3-hydroxypropionate (3-HP), 3-hydroxyhexanoate (3-HH), 3-hydroxyvalerate (3-HV), 4-hydroxyvalerate (4-HV), 5-hydroxyvalerate (5-HV), and 6-hydroxyhexanoate (6-HH).

Specifically, the copolymerized PHA may comprise a 4-HB repeat unit and further comprises one or more repeat units selected from the group consisting of a 3-HB repeat unit, a 3-HP repeat unit, a 3-HH repeat unit, a 3-HV repeat unit, a 4-HV repeat unit, a 5-HV repeat unit, and a 6-HH repeat unit. More specifically, the PHA may comprise a 4-HB repeat unit and a 3-HB repeat unit.

For example, the copolymerized PHA may comprise the 3-HB repeat unit in an amount of 20% by weight or more, 35% by weight or more, 40% by weight or more, 50% by weight or more, 60% by weight or more, 70% by weight or more, or 75% by weight or more, and 99% by weight or less, 98% by weight or less, 97% by weight or less, 96% by weight or less, 95% by weight or less, 93% by weight or less, 91% by weight or less, 90% by weight or less, 80% by weight or less, 70% by weight or less, 60% by weight or less, or 55% by weight or less, based on the total weight of the copolymerized PHA.

The PHA whose crystallinity is adjusted may be one in which its crystallinity and amorphousness are adjusted as the irregularities are increased in its molecular structure. Specifically, the types or ratios of the monomers or the types or contents of the isomers may be adjusted.

According to an embodiment of the present invention, the PHA may comprise two or more types of PHA having different crystallinities. Specifically, the PHA may be prepared by mixing two or more types of PHA having different crystallinities to have the content of a 4-HB repeat unit in the specific range.

Specifically, the PHA may comprise a first PHA that is a semi-crystalline PHA.

As a semi-crystalline PHA (hereinafter, referred to as scPHA) with controlled crystallinity, the first PHA may comprise a 4-HB repeat unit in an amount of 0.1% by weight to 30% by weight. For example, the first PHA may comprise a 4-HB repeat unit in an amount of 0.1% by weight to 30% by weight, 0.5% by weight to 30% by weight, 1% by weight to 30% by weight, 3% by weight to 30% by weight, 1% by weight to 28% by weight, 1% by weight to 25% by weight, 1% by weight to 24% by weight, 1% by weight to 15% by weight, 2% by weight to 25% by weight, 3% by weight to 25% by weight, 3% by weight to 24% by weight, 5% by weight to 24% by weight, 7% by weight to 20% by weight, 10% by weight to 20% by weight, 15% by weight to 25% by weight, or 15% by weight to 24% by weight.

The glass transition temperature (Tg) of the first PHA may be −30° C. to 80° C., −30° C. to 10° C., −25° C. to 5° C., −25° C. to 0° C., −20° C. to 0° C., or −15° C. to 0° C. The crystallization temperature (Tc) of the first PHA may be 70° C. to 120° C., 75° C. to 120° C., or 75° C. to 115° C. The melting temperature (Tm) of the first PHA may be 105° C. to 165° C., 110° C. to 160° C., 115° C. to 155° C., or 120° C. to 150° C.

The first PHA may have a weight average molecular weight of 10,000 g/mole to 1,200,000 g/mole, 50,000 g/mole to 1,100,000 g/mole, 100,000 g/mole to 1,000,000 g/mole, 100,000 g/mole to 900,000 g/mole, 200,000 g/mole to 800,000 g/mole, 200,000 g/mole to 600,000 g/mole, or 200,000 g/mole to 400,000 g/mole.

In addition, the PHA may comprise a second PHA, which is an amorphous PHA resin with controlled crystallinity.

As an amorphous PHA (hereinafter, referred to as aPHA) with controlled crystallinity, the second PHA may comprise a 4-HB repeat unit in an amount of 15% by weight to 60% by weight, 15% by weight to 55% by weight, 20% by weight to 55% by weight, 25% by weight to 55% by weight, 30% by weight to 55% by weight, 35% by weight to 55% by weight, 20% by weight to 50% by weight, 25% by weight to 50% by weight, 30% by weight to 50% by weight, 35% by weight to 50% by weight, or 20% by weight to 40% by weight.

The glass transition temperature (Tg) of the second PHA may be −45° C. to −10° C., −35° C. to −15° C., −35° C. to −20° C., or −30° C. to −20° C.

In addition, the crystallization temperature (Tc) of the second PHA may not be measured or may be 60° C. to 120° C., 60° C. to 110° C., 70° C. to 120° C., or 75° C. to 115° C. The melting temperature (Tm) of the second PHA may not be measured or may be 100° C. to 170° C., 100° C. to 160° C., 110° C. to 160° C., or 120° C. to 150° C.

The second PHA resin may have a weight average molecular weight of 10,000 g/mole to 1,200,000 g/mole, 10,000 g/mole to 1,000,000 g/mole, 50,000 g/mole to 1,000,000 g/mole, 200,000 g/mole to 1,200,000 g/mole, 300,000 g/mole to 1,000,000 g/mole, 100,000 g/mole to 900,000 g/mole, 500,000 g/mole to 900,000 g/mole, 200,000 g/mole to 800,000 g/mole, or 200,000 g/mole to 400,000 g/mole.

The first PHA and the second PHA may be distinguished in terms of the content of a 4-HB repeat unit and may have at least one characteristic selected from the group consisting of the above glass transition temperature (Tg), crystallization temperature (Tc), and melting temperature (Tm). Specifically, the first PHA and the second PHA may be distinguished in terms of the content of a 4-HB repeat unit, glass transition temperature (Tg), crystallization temperature (Tg), melting temperature (Tm), and the like.

According to an embodiment of the present invention, the PHA may comprise the first PHA, or it may comprise both the first PHA and the second PHA.

Specifically, as the PHA comprises the first PHA, which is a semi-crystalline PHA, or both the first PHA, which is a semi-crystalline PHA, and the second PHA, which is an amorphous PHA, more specifically, as the contents of the first PHA and the second PHA are adjusted, it is possible to more effectively control the yield of the desired material.

In addition, the glass transition temperature (Tg) of the PHA may be −45° C. to 80° C., −35° C. to 80° C., −30° C. to 80° C., −25° C. to 75° C., −20° C. to 70° C., −35° C. to 5° C., −25° C. to 5° C., −35° C. to 0° C., −25° C. to 0° C., −30° C. to −10° C., −35° C. to −15° C., −35° C. to −20° C., −20° C. to 0° C., −15° C. to 0° C., or −15° C. to −5° C.

The crystallization temperature (Tc) of the PHA may not be measured or may be 60° C. to 120° C., 60° C. to 110° C., 70° C. to 120° C., 75° C. to 120° C., 75° C. to 115° C., 75° C. to 110° C., or 90° C. to 110° C.

The melting temperature (Tm) of the PHA may not be measured or may be 100° C. to 170° C., 105° C. to 170° C., 105° C. to 165° C., 110° C. to 160° C., 115° C. to 155° C., 110° C. to 150° C., 120° C. to 150° C., or 120° C. to 140° C.

In addition, the PHA may have a weight average molecular weight of 10,000 g/mole to 1,200,000 g/mole. For example, the weight average molecular weight of the PHA resin may be 50,000 g/mole to 1,200,000 g/mole, 100,000 g/mole to 1,200,000 g/mole, 50,000 g/mole to 1,000,000 g/mole, 100,000 g/mole to 1,000,000 g/mole, 200,000 g/mole to 1,200,000 g/mole, 250,000 g/mole to 1,150,000 g/mole, 300,000 g/mole to 1,100,000 g/mole, 350,000 g/mole to 1,000,000 g/mole, 350,000 g/mole to 950,000 g/mole, 100,000 g/mole to 900,000 g/mole, 200,000 g/mole to 800,000 g/mole, 200,000 g/mole to 700,000 g/mole, 250,000 g/mole to 650,000 g/mole, 200,000 g/mole to 400,000 g/mole, 300,000 g/mole to 800,000 g/mole, 300,000 g/mole to 600,000 g/mole, 500,000 g/mole to 1,200,000 g/mole, 500,000 g/mole to 1,000,000 g/mole 550,000 g/mole to 1,050,000 g/mole, 550,000 g/mole to 900,000 g/mole, 600,000 g/mole to 900,000 g/mole, or 500,000 g/mole to 900,000 g/mole.

The PHA may have a crystallinity of 90% or less as measured by a differential scanning calorimeter (DSC). For example, the crystallinity of the PHA may be measured by differential scanning calorimetry and may be 90% or less, 85% or less, 80% or less, 75% or less, or 70% or less.

In addition, the PHA may have an average particle size of 0.5 μm to 5 μm. For example, the PHA may have an average particle size of 0.5 μm to 5 μm, 0.5 μm to 4.5 μm, 0.7 μm to 4 μm, 1 μm to 3.5 μm, or 1.2 μm to 3.5 μm.

The average particle size of the PHA may be measured with a nano particle size analyzer (e.g., Zetasizer Nano ZS). Specifically, the PHA is subjected to measurement of average particle size through dynamic light scattering (DLS) at a temperature of 25° C. and a measurement angle of 175° using Zetasizer Nano ZS (manufacturer: Marven). In such an event, the value of the peak derived through the polydispersity index (PDI) in the confidence interval of 0.5 is taken as the particle size.

The PHA may have a polydispersity index (PDI) of less than 2.5. For example, the polydispersity index of the PHA may be less than 2.5, 2.3 or less, 2.1 or less, or 2.0 or less.

As the average particle size and polydispersity index of the PHA each satisfy the above ranges, it is possible to more effectively control the yield of the desired material.

In addition, the PHA may be obtained by cell disruption using a non-mechanical method or a chemical method. Specifically, since the PHA is a natural thermoplastic polyester polymer that accumulates in microbial cells and has a relatively large average particle size, it may be obtained through a disruption process in order to more effectively control the yield of the desired material and enhance the process efficiency.

The process for preparing tetrahydrofuran, gamma-butyrolactone, or 1,4-butanediol according to an embodiment of the present invention is carried out through a hydrogenation reaction using a polyhydroxyalkanoate (PHA).

Specifically, the hydrogenation reaction may be carried out using a copper-based catalyst in an aprotic solvent. More specifically, the hydrogenation reaction may be carried out using a PHA, an aprotic solvent, and a copper-based catalyst in the presence of hydrogen.

The hydrogenation reaction may be carried out at a temperature of 50° C. to 500° C. and a pressure of 1 bar to 100 bar. For example, the hydrogenation reaction may be carried out at a temperature of 55° C. to 480° C., 80° C. to 460° C., 100° C. to 420° C., 150° C. to 400° C., 200° C. to 360° C., 220° C. to 350° C., 250° C. to 350° C., 270° C. to 310° C., 275° C. to 300° C., 280° C. to 290° C., 50° C. to 300° C., 80° C. to 250° C., 100° C. to 220° C., 120° C. to 205° C., 155° C. to 200° C., or 175° C. to 195° C., and a pressure of 5 bar to 75 bar, 10 bar to 100 bar, 10 bar to 65 bar, 1 bar to 55 bar, 5 bar to 35 bar, 10 bar to 30 bar, 15 bar to 55 bar, 30 bar to 90 bar, 45 bar to 80 bar, or 45 bar to 65 bar. As the temperature and pressure of the hydrogenation reaction are each controlled within the above ranges, it is possible to selectively control the yield of the desired material, to improve process stability, and to reduce process cost.

According to another embodiment of the present invention, hydrogen gas is injected in the hydrogenation reaction step, and the hydrogen gas may be injected in a mole number of 1 time to 500 times the number of moles of the polyhydroxyalkanoate (PHA) monomer.

Specifically, the hydrogenation reaction can be carried out in the presence of hydrogen. More specifically, it may be carried out by injecting hydrogen gas in the hydrogenation reaction step.

For example, in the hydrogenation reaction step, hydrogen gas may be injected at 1 time to 350 times, 2 times to 250 times, 5 times to 100 times, 10 times to 80 times, or 30 times to 60 times the number of moles of the polyhydroxyalkanoate (PHA) monomer.

The aprotic solvent may comprise at least one selected from the group consisting of acetone, dioxane, methyl acetate, ethyl acetate, N,N-dimethylformamide, N,N-dimethylacetamide, N-methylpyrrolidone, acetonitrile, propionitrile, butyronitrile, benzonitrile, acrylonitrile, dimethylsulfoxide, dichloromethane, dimethylpropylene urea, and hexamethylphosphate triamide. The aprotic solvent may be selectively used depending on the desired material.

In addition, the copper-based catalyst may be a catalyst supported on a support. Specifically, the copper-based catalyst is supported on a support, and the support may comprise at least one selected from the group consisting of carbon, zeolite, $Al_2O_3$, $SiO_2$, $TiO_2$, $ZrO_2$, MgO, and $Cr_2O_3$.

In addition, the copper-based catalyst may be a copper catalyst or a copper-metal composite catalyst, and the copper-metal composite catalyst may comprise copper-metal complex which comprise at least one metal selected from the group consisting of Mn, Zn, Mg Co, Ni, Cr, and Fe, other than copper.

More specifically, the copper-based catalyst is a copper-based catalyst supported on a support. The support may be $Al_2O_3$, $SiO_2$, $TiO_2$, or $ZrO_2$, and the copper-based catalyst may be a Cu catalyst, a Cu—Mn catalyst, a Cu—Zn catalyst, or a Cu—Mg catalyst. For example, the copper-based catalyst may be $Cu/Al_2O_3$, $CuZn/Al_2O_3$, $CuMn/Al_2O_3$, $Cu/SiO_2$, $Cu/ZrO_2$, $Cu/TiO_2$, $CuMn/SiO_2$, $CuMn/ZrO_2$, or $CuMn/TiO_2$, but it is not limited thereto.

In addition, the content of copper or a copper-metal composite in the copper-based catalyst supported on the support may be 0.1% by weight to 85% by weight based on the total weight of the support. For example, the copper-based catalyst may be a catalyst supported with 85% by weight or less of copper or a copper-metal composite based on the total weight of the support. More specifically, the content of copper or a copper-metal composite may be 80% by weight or less, 75% by weight or less, 70% by weight or less, 65% by weight or less, 64% by weight or less, 30% by weight or less, 10% by weight or less, 8% by weight or less, 7% by weight or less, 6% by weight or less, or 5.5% by weight or less, and 0.1% by weight or more, 0.5% by weight or more, 1.5% by weight or more, or 2% by weight or more, or 0.1% by weight to 85% by weight, 0.5% by weight to 75% by weight, 1% by weight to 70% by weight, 2% by weight to 68% by weight, 5% by weight to 66% by weight, 8% by weight to 64% by weight, 0.1% by weight to 25% by weight, 0.2% by weight to 20% by weight, 0.5% by weight to 13% by weight, 1% by weight to 10% by weight, 1.5% by weight to 8% by weight, or 2% by weight to 5% by weight, based on the total weight of the support.

The copper-based catalyst may have an average particle diameter of 10 μm to 2,000 μm. For example, the average particle diameter of the copper-based catalyst may be 25 μm to 1,500 μm, 50 μm to 1,000 μm, 100 μm to 800 μm, or 200 μm to 500 μm.

In addition, the copper-based catalyst may have a surface area of 500 $m^2/g$ or less. For example, the surface area of the copper-based catalyst may be 350 $m^2/g$ or less, 300 $m^2/g$ or less, 100 $m^2/g$ or less, or 80 $m^2/g$ or less.

Batch Reaction

The process for preparing tetrahydrofuran, gamma-butyrolactone, or 1,4-butanediol according to an embodiment of the present invention may comprise mixing a polyhydroxyalkanoate (PHA) and a copper-based catalyst with an aprotic solvent; and subjecting the mixture to a hydrogenation reaction.

In addition, prior to the hydrogenation reaction step, it may comprise removing oxygen in the reactor; and adjusting the internal pressure of the reactor to 1 bar to 100 bar by injecting hydrogen gas. The removal of oxygen may be carried out using hydrogen gas, but it is not limited thereto.

The injection amount of hydrogen gas may be 1 time to 500 times the weight of the polyhydroxyalkanoate (PHA). For example, the injection amount of hydrogen gas may be 1 time to 350 times, 2 times to 250 times, 5 times to 100 times, 10 times to 80 times, or 30 times to 60 times the weight of the polyhydroxyalkanoate (PHA) monomer.

In addition, the weight ratio of the polyhydroxyalkanoate (PHA) to the copper-based catalyst may be 1:0.01 to 5. For example, the weight ratio of the polyhydroxyalkanoate (PHA) to the copper-based catalyst may be 1:0.02 to 4.5, 1:0.05 to 2.5, 1:0.08 to 2.2, 1:0.1 to 2, 1:0.1 to 1.2, 1:0.1 to 1, 1:0.1 to 0.8, 1:0.1 to 4, 1:0.5 to 3.5, 1:1 to 3, 1:1.2 to 2.5, or 1:1.5 to 2.2. As the weight ratio of the polyhydroxyalkanoate (PHA) to the copper-based catalyst is adjusted within the above range, the yield of the desired material can be effectively controlled.

In addition, the hydrogenation reaction may be carried out at a stirring speed of 200 rpm to 2,000 rpm for 1 hour to 10 hours. For example, the stirring speed may be 250 rpm to 1,500 rpm, 300 rpm to 1,200 rpm, 400 rpm to 1,000 rpm, 450 rpm to 900 rpm, 500 rpm to 750 rpm, or 520 rpm to 700 rpm; and the reaction time may be 1 hour to 9 hours, 2 hours to 7.5 hours, 4.5 hours to 7 hours, or 5.5 hours to 6.5 hours.

Continuous Reaction

The process for preparing tetrahydrofuran, gamma-butyrolactone, or 1,4-butanediol according to another embodiment of the present invention may comprise dissolving a polyhydroxyalkanoate (PHA) in an aprotic solvent; and passing the dissolved polyhydroxyalkanoate (PHA) through a catalyst bed comprising a copper-based catalyst to subject it to a hydrogenation reaction.

The dissolution step may be a step of dissolving a PHA in an aprotic solvent to be 0.1% by weight to 30% by weight. For example, the content of dissolved PHA may be 0.1% by weight to 20% by weight, 0.2% by weight to 16% by weight, 0.5% by weight to 10% by weight, 0.6% by weight to 8% by weight, 0.7% by weight to 6% by weight, 0.8% by weight to 3% by weight, or 0.9% by weight to 2% by weight.

In addition, in the continuous reaction, the weight hourly space velocity (WHSV) of the copper-based catalyst relative to the polyhydroxyalkanoate (PHA) may be 0.1 $h^{-1}$ to 10 $h^{-1}$. For example, the weight hourly space velocity (WHSV) of the copper-based catalyst relative to the polyhydroxyalkanoate (PHA) may be 0.02 $h^{-1}$ to 5 $h^{-1}$, 0.05 $h^{-1}$ to 2 $h^{-1}$, 0.1 $h^{-1}$ to 1 $h^{-1}$, or 0.2 $h^{-1}$ to 0.5 $h^{-1}$.

According to an embodiment of the present invention, the yield of tetrahydrofuran, gamma-butyrolactone, or 1,4-butanediol may exceed 65% by mole. For example, the yield of tetrahydrofuran, gamma-butyrolactone, or 1,4-butanediol may be 67% by mole or more, 69% by mole or more, 70% by mole or more, 71% by mole or more, 80% by mole or more, 85% by mole or more, 90% by mole or more, 91% by mole or more, 93% by mole or more, 95% by mole or more, 97% by mole or more, or 99% by mole or more. The yield may be measured using gas chromatography (GC) for a final product obtained through the hydrogenation reaction.

Specifically, the yield of tetrahydrofuran may exceed 65% by mole. For example, the yield of tetrahydrofuran may be 67% by mole or more, 69% by mole or more, 70% by mole or more, 71% by mole or more, 80% by mole or more, 95% by mole or more, or 97% by mole or more.

More specifically, when the copper-based catalyst is $Cu/Al_2O_3$ or $CuMn/Al_2O_3$ supported with 6% by weight to 85% by weight of copper, the yield of tetrahydrofuran may exceed 65% by mole. For example, when the copper-based catalyst is a $Cu/Al_2O_3$ or $CuMn/Al_2O_3$ catalyst containing copper in an amount of 6% by weight to 80% by weight, 7% by weight to 75% by weight, 6% by weight to 65% by weight, or 8% by weight to 64% by weight, the yield of tetrahydrofuran may exceed 65% by mole.

In addition, when the hydrogenation reaction is carried out at a temperature of 55° C. to 480° C., 80° C. to 460° C., 100° C. to 420° C., 150° C. to 400° C., 200° C. to 360° C., 220° C. to 350° C., 250° C. to 350° C., 270° C. to 310° C., 275° C. to 300° C., or 280° C. to 290° C., and a pressure of 10 bar to 100 bar, 30 bar to 90 bar, 45 bar to 80 bar, or 45 bar to 65 bar, the yield of tetrahydrofuran may exceed 65% by mole.

Alternatively, the yield of gamma-butyrolactone may exceed 65% by mole. For example, the yield of gamma-butyrolactone may be 67% by mole or more, 69% by mole or more, 70% by mole or more, 80% by mole or more, 85% by mole or more, 95% by mole or more, or 99% by mole or more.

Specifically, when the hydrogenation reaction is carried out at a pressure of 1 bar to 75 bar, the yield of gamma-butyrolactone may exceed 65% by mole. For example, when the hydrogenation reaction is carried out at 5 bar to 75 bar, 10 bar to 65 bar, 15 bar to 55 bar, 1 bar to 35 bar, 10 bar to 25 bar, 30 bar to 65 bar, or 45 bar to 55 bar, the yield of gamma-butyrolactone may exceed 65% by mole.

In addition, when the support of the copper-based catalyst comprises $SiO_2$ or $TiO_2$, the yield of gamma-butyrolactone may exceed 65% by mole.

In addition, when the catalyst is a $Cu/Al_2O_3$ catalyst supported with copper in an amount of less than 8% by weight, the yield of gamma-butyrolactone may exceed 65% by mole. For example, when the catalyst is a $Cu/Al_2O_3$ catalyst supported with copper in an amount of less than 8% by weight, 7% by weight or less, 6% by weight or less, 0.1% by weight to 7% by weight, 0.5% by weight to 8% by weight, 1% by weight to 6% by weight, or 1.5% by weight to 5.5% by weight, the yield of gamma-butyrolactone may exceed 65% by mole.

Alternatively, the yield of 1,4-butanediol may exceed 65% by mole. For example, the yield of 1,4-butanediol may be 70% by mole or more, 85% by mole or more, 90% by mole or more, 91% by mole or more, or 93% by mole or more.

For example, when the hydrogenation reaction is carried out at a temperature of 50° C. to 300° C., 80° C. to 250° C., 100° C. to 220° C., 120° C. to 205° C., 155° C. to 200° C., or 175° C. to 195° C., and a pressure of 10 bar to 100 bar, 30 bar to 90 bar, 45 bar to 80 bar, or 45 bar to 65 bar, the yield of 1,4-butanediol may exceed 65% by mole.

According to another embodiment of the present invention, it may further comprise pretreating the polyhydroxyalkanoate (PHA) prior to the hydrogenation reaction.

Specifically, the pretreatment step may comprise purifying it using a solvent extraction method. The solvent extraction method may be carried out using one or more solvents selected from the group consisting of dioxane, chloroform, and methylene chloride.

For example, the solvent extraction method may be carried out by mixing a PHA, that is, dry matter obtained from a PHA culture medium or fermentation broth with the solvent to extract a PHA, separating cell residues, and then adding it dropwise to ethanol to recover it.

In addition, after the hydrogenation reaction, it may further comprise treating the reaction product with one or more steps selected from the group consisting of a distillation step, an ion exchange step, a solvent extraction step, and an adsorption step. As these treatment steps are additionally carried out, the yield can be more effectively controlled.

The distillation may be carried out using a commonly used distillation method. The ion exchange, solvent extraction, and adsorption may each be carried out using a commonly used method as long as the effects of the present invention are not impaired.

For example, the distillation may be carried out by heating the reaction product using a receiver of a distillation column, condensing vapor generated from the top of the distillation column with a condenser to separate the product, and recovering the product.

The distillation may be carried out at a temperature of 50° C. to 250° C. and a reduced pressure of 10 Torr to 760 Torr. For example, the distillation may be carried out at a temperature of 50° C. to 200° C. or 80° C. to 200° C. and a reduced pressure of 20 Torr to 700 Torr or 30 Torr to 500 Torr.

MODE FOR THE INVENTION

Hereinafter, the present invention will be described in more detail with reference to the following examples. But the following Examples are intended to illustrate the present invention, and the scope of the Examples is not limited thereto only.

EXAMPLE

Preparation of Polyhydroxyalkanoate (PHA) Pellets

Preparation Example 1-1

400 ml of a polyhydroxyalkanoate (PHA) culture medium was stirred at 3,800 rpm for 20 minutes using a high-speed centrifuge to remove the supernatant. Thereafter, 400 ml of distilled water was added and mixed, and the supernatant was removed once more using a high-speed centrifuge under the same conditions. Thereafter, it was freeze-dried at −70° C. and vacuum and uniformly pulverized to an average particle size of 1 μm using a homogenizer (product name: Homomixer Mark2, manufacturer: Primix).

50 g of the pulverized material was mixed with 1 liter of chloroform (manufacturer: Daejung Chemicals & Metals), which was stirred at 55° C. for 1.5 hours. The cell residues were removed by filtration, and the chloroform filtrate was added dropwise to 5 liters of ethanol. Thereafter, the precipitated PHA was recovered and dried in a vacuum oven at 40° C. to prepare PHA pellets (recovery: 90%, purity: 99%, content of 4-hydroxybutyrate (4-HB): 100% by weight).

Preparation of a Catalyst

Preparation Example 2-1: Preparation of a $Cu/Al_2O_3$ Catalyst 250 ml of an aqueous solution in which 5 g of alumina ($Al_2O_3$, Strem) and 1.52 g of copper nitrate trihydrate ($Cu(NO_3)_2 \cdot 3H_2O$, manufacturer: Daejung Chemicals & Metals) had been dissolved was stirred at room temperature for 10 hours to prepare a slurry. The solvent in the slurry was removed using a vacuum rotary evaporator, it was then dried in a circulation oven maintained at 105° C. for 12 hours.

Thereafter, the dried copper-alumina composite was calcined at 500° C. for 4 hours under an air atmosphere and then reduced at 500° C. for 2 hours under a 5% hydrogen and nitrogen atmosphere. Thereafter, it was sufficiently cooled at room temperature and stabilized for 0.5 hour under a 1% oxygen and nitrogen atmosphere to prepare a $Cu/Al_2O_3$ catalyst in which 8% by weight of copper was supported on an alumina support.

Preparation Example 2-2: Preparation of a $Cu/Al_2O_3$ Catalyst

A $Cu/Al_2O_3$ catalyst in which 2% by weight of copper was supported was prepared in the same manner as in Preparation Example 2-1, except that 0.38 g of copper nitrate trihydrate ($Cu(NO_3)_2 \cdot 3H_2O$, manufacturer: Daejung Chemicals & Metals) was used.

Preparation Example 2-3: Preparation of a $Cu/Al_2O_3$ Catalyst

A $Cu/Al_2O_3$ catalyst in which 5% by weight of copper was supported was prepared in the same manner as in Preparation Example 2-1, except that 0.95 g of copper nitrate trihydrate ($Cu(NO_3)_2 \cdot 3H_2O$, manufacturer: Daejung Chemicals & Metals) was used.

Preparation Example 2-4: Preparation of a $Cu/Al_2O_3$ Catalyst

A $Cu/Al_2O_3$ catalyst in which 16% by weight of copper was supported was prepared in the same manner as in Preparation Example 2-1, except that 3.04 g of copper nitrate trihydrate ($Cu(NO_3)_2 \cdot 3H_2O$, manufacturer: Daejung Chemicals & Metals) was used.

Preparation Example 2-5: Preparation of a $Cu/Al_2O_3$ Catalyst

A $Cu/Al_2O_3$ catalyst in which 32% by weight of copper was supported was prepared in the same manner as in Preparation Example 2-1, except that 6.08 g of copper nitrate trihydrate ($Cu(NO_3)_2 \cdot 3H_2O$, manufacturer: Daejung Chemicals & Metals) was used.

Preparation Example 2-6: Preparation of a $Cu/Al_2O_3$ Catalyst

A $Cu/Al_2O_3$ catalyst in which 64% by weight of copper was supported was prepared in the same manner as in Preparation Example 2-1, except that 12.16 g of copper nitrate trihydrate ($Cu(NO_3)_2 \cdot 3H_2O$, manufacturer: Daejung Chemicals & Metals) was used.

Preparation Example 2-7: Preparation of a $CuZn/Al_2O_3$ Catalyst

A $CuZn/Al_2O_3$ catalyst in which 8% by weight of copper and 8% by weight of zinc were supported on an alumina support was prepared in the same manner as in Preparation Example 2-1, except that 1.8 g of zinc precursor zinc nitrate hexahydrate ($Zn(NO_3)_2 \cdot 6H_2O$, manufacturer: Sigma-Aldrich) was additionally used.

Preparation Example 2-8: Preparation of a $CuMn/Al_2O_3$ Catalyst

A $CuMn/Al_2O_3$ catalyst in which 8% by weight of copper and 8% by weight of manganese were supported on an alumina support was prepared in the same manner as in Preparation Example 2-1, except that 2.1 g of manganese precursor manganese nitrate hexahydrate ($Mn(NO_3)_2 \cdot 6H_2O$, manufacturer: Junsei) was additionally used.

Preparation Example 2-9: Preparation of a $Cu/SiO_2$ Catalyst

A $Cu/SiO_2$ catalyst in which 8% by weight of copper was supported on a silica support was prepared in the same manner as in Preparation Example 2-1, except that silica ($SiO_2$, manufacturer: Strem) was used instead of alumina.

Preparation Example 2-10: Preparation of a $Cu/ZrO_2$ Catalyst

A $Cu/ZrO_2$ catalyst in which 8% by weight of copper was supported on a zirconia support was prepared in the same manner as in Preparation Example 2-1, except that zirconia ($ZrO_2$, manufacturer: Sigma-Aldrich) was used instead of alumina.

Preparation Example 2-11: Preparation of a $Cu/TiO_2$ Catalyst

A $Cu/TiO_2$ catalyst in which 8% by weight of copper was supported on a titania support was prepared in the same manner as in Preparation Example 2-1, except that titania ($TiO_2$, manufacturer: Sigma-Aldrich) was used instead of alumina.

Preparation Example 2-12: Preparation of a $CuMn/SiO_2$ Catalyst

A $CuMn/SiO_2$ catalyst in which 8% by weight of copper and 8% by weight of manganese were supported on a silica support was prepared in the same manner as in Preparation Example 2-7, except that 2.1 g of manganese precursor manganese nitrate hexahydrate ($Mn(NO_3)_2 \cdot 6H_2O$, manufacturer: Junsei) was additionally used.

Preparation Example 2-13: Preparation of a $CuMn/ZrO_2$ Catalyst

A $CuMn/ZrO_2$ catalyst in which 8% by weight of copper and 8% by weight of manganese were supported on a zirconia support was prepared in the same manner as in Preparation Example 2-8, except that 2.1 g of manganese precursor manganese nitrate hexahydrate ($Mn(NO_3)_2 \cdot 6H_2O$, manufacturer: Junsei) was additionally used.

Preparation Example 2-14: Preparation of a $CuMn/TiO_2$ Catalyst

A $CuMn/TiO_2$ catalyst in which 8% by weight of copper and 8% by weight of manganese were supported on a titania support was prepared in the same manner as in Preparation Example 2-9, except that 2.1 g of manganese precursor manganese nitrate hexahydrate ($Mn(NO_3)_2 \cdot 6H_2O$, manufacturer: Junsei) was additionally used.

Preparation of a Product Using a Hydrogenation Reaction

Example 1-1

An autoclave reactor was charged with 1 g of the PHA pellets prepared in Preparation Example 1-1, 40 g of dioxane, and 0.5 g of the $Cu/Al_2O_3$ catalyst prepared in Preparation Example 2-1, and oxygen inside the reactor was removed three or four times using hydrogen gas. Thereafter, hydrogen gas was injected to raise the pressure to 50 bar, and it was heated to the reaction temperature of 280° C. The time when the reaction temperature was reached was set as the reaction initiation time, and the reaction was carried out for 6 hours in total at a stirring speed of 600 rpm. Upon completion of the reaction, the temperature was lowered to room temperature, the final product was recovered, and the yield of the final product was analyzed using gas chromatography (GC). The results are shown in Table 2.

Examples 1-2 to 1-14 and Comparative Examples 1-1 to 1-7

Final products were recovered in the same manner as in Example 1-1, except that the components and process conditions were changed as shown in Table 1 below. Thereafter, the yield of the final product was analyzed using gas chromatography (GC). The results are shown in Table 2. Here, in Comparative Example 1-1, pretreated succinic anhydride (trade name: succinic anhydride, manufacturer: Sigma-Aldrich) was used.

TABLE 1

| | Resin | Catalyst Type | Catalyst Content (g) | Solvent | Temp. (° C.) | Pressure (bar) |
|---|---|---|---|---|---|---|
| Ex. 1-1 | Prep. Ex. 1-1 | Prep. Ex. 2-1 | 0.5 | Dioxane | 280 | 50 |
| Ex. 1-2 | Prep. Ex. 1-1 | Prep. Ex. 2-1 | 0.1 | Dioxane | 280 | 50 |
| Ex. 1-3 | Prep. Ex. 1-1 | Prep. Ex. 2-1 | 0.1 | Dioxane | 310 | 50 |
| Ex. 1-4 | Prep. Ex. 1-1 | Prep. Ex. 2-1 | 0.1 | Dioxane | 280 | 80 |
| Ex. 1-5 | Prep. Ex. 1-1 | Prep. Ex. 2-4 | 0.1 | Dioxane | 280 | 50 |
| Ex. 1-6 | Prep. Ex. 1-1 | Prep. Ex. 2-5 | 0.1 | Dioxane | 280 | 50 |

TABLE 1-continued

| | Resin | Catalyst Type | Catalyst Content (g) | Solvent | Temp. (° C.) | Pressure (bar) |
|---|---|---|---|---|---|---|
| Ex. 1-7 | Prep. Ex. 1-1 | Prep. Ex. 2-6 | 0.1 | Dioxane | 280 | 50 |
| Ex. 1-8 | Prep. Ex. 1-1 | Prep. Ex. 2-8 | 0.1 | Dioxane | 280 | 50 |
| Ex. 1-9 | Prep. Ex. 1-1 | Prep. Ex. 2-1 | 0.1 | Dioxane | 220 | 50 |
| Ex. 1-10 | Prep. Ex. 1-1 | Prep. Ex. 2-1 | 0.1 | Dioxane | 280 | 20 |
| Ex. 1-11 | Prep. Ex. 1-1 | Prep. Ex. 2-11 | 0.1 | Dioxane | 280 | 50 |
| Ex. 1-12 | Prep. Ex. 1-1 | Prep. Ex. 2-2 | 0.1 | Dioxane | 280 | 50 |
| Ex. 1-13 | Prep. Ex. 1-1 | Prep. Ex. 2-14 | 0.1 | Dioxane | 280 | 50 |
| Ex. 1-14 | Prep. Ex. 1-1 | Prep. Ex. 2-12 | 0.1 | Dioxane | 190 | 50 |
| C. Ex. 1-1 | Succinic anhydride | Prep. Ex. 2-1 | 0.1 | Dioxane | 280 | 50 |
| C. Ex. 1-2 | Prep. Ex. 1-1 | Prep. Ex. 2-1 | 0.1 | Ethanol | 280 | 50 |

TABLE 2

| | Yield of a product (% by mole) Tetrahydrofuran | Gamma-butyrolactone | 1,4-Butanediol | Butanol |
|---|---|---|---|---|
| Ex. 1-1 | 97.1 | 1.3 | 0.2 | 1.2 |
| Ex. 1-2 | 71.2 | 27.2 | 0.8 | 0.5 |
| Ex. 1-3 | 95.5 | 0.7 | 0.0 | 3.0 |
| Ex. 1-4 | 80.8 | 0.5 | 15.7 | 2.4 |
| Ex. 1-5 | 73.3 | 25.6 | 0.4 | 0.6 |
| Ex. 1-6 | 74.3 | 23.4 | 0.6 | 0.8 |
| Ex. 1-7 | 73.2 | 10.3 | 0.7 | 14.9 |
| Ex. 1-8 | 81.2 | 12.2 | 5.6 | 0.7 |
| Ex. 1-9 | 16.1 | 80.6 | 3.1 | 0.0 |
| Ex. 1-10 | 12.8 | 87.2 | 0.0 | 0.0 |
| Ex. 1-11 | 0.0 | 99.9 | 0.0 | 0.0 |
| Ex. 1-12 | 30.2 | 69.1 | 0.3 | 0.3 |
| Ex. 1-13 | 18.9 | 70.1 | 10.5 | 0.0 |
| Ex. 1-14 | 0.0 | 5.4 | 93.5 | 0.0 |
| C. Ex. 1-1 | 65.0 | 30.1 | 4.3 | 0.1 |
| C. Ex. 1-2 | 33.5 | 29.0 | 0.0 | 0.0 |

As can be seen from Table 2 above, as the PHA pellets, aprotic solvent, and catalyst were reacted in the presence of hydrogen while the process temperature and pressure and the content of copper supported on the catalyst were adjusted and the carrier of the catalyst was selectively controlled, the yield of hydrofuran, gamma-butyrolactone, or 1,4-butanediol could be adjusted to exceed 65% by mole.

In particular, in Comparative Example 1-2 in which ethanol was used instead of an aprotic solvent, the yields of tetrahydrofuran, gamma-butyrolactone, and 1,4-butanediol were all very low due to side reactions.

Example 2-1

A continuous fixed bed reactor made of SUS316 was packed with 2.0 g of the catalyst prepared in Preparation Example 2-7 to form a catalyst bed, and glass fibers were placed on and under the catalyst bed to fix the catalyst bed. Thereafter, the catalyst was activated by flowing hydrogen gas at 300° C. for 2 hours. Thereafter, the flow rate of hydrogen gas was increased to raise the pressure inside the reactor to 40 bar, and the temperature was then adjusted to 280° C.

Thereafter, the PHA pellets prepared in Preparation Example 1-1 were dissolved at 1% by weight in dioxane, the solution was fed to the reactor at a rate of 1 ml/minute, and, at the same time, hydrogen gas was supplied thereto at a rate of 50 times the number of moles of the polyhydroxyalkanoate (PHA) monomer to carry out the reaction. The product was recovered every hour, and the yield was analyzed using gas chromatography (GC). The results are shown in Table 3.

Example 2-2

The reaction was carried out in the same manner as in Example 2-1, except that the catalyst prepared in Preparation Example 2-1 was used. The product was recovered every hour, and the yield was analyzed using gas chromatography (GC). The results are shown in Table 3.

TABLE 3

| | | Yield of a product (% by mole) | |
|---|---|---|---|
| | Reaction time | Tetrahydrofuran | Gamma-butyrolactone |
| Ex. 2-1 | 1 | 98.6 | 0.2 |
| | 2 | 98.4 | 0.3 |
| | 3 | 98.3 | 0.5 |
| | 4 | 98.1 | 0.6 |
| | 5 | 98.1 | 0.6 |
| | 6 | 98.0 | 0.8 |
| | 7 | 98.1 | 0.7 |
| | 8 | 97.8 | 0.8 |
| | 9 | 97.6 | 0.7 |
| | 10 | 97.5 | 0.9 |
| | 11 | 97.7 | 1.1 |
| | 12 | 97.5 | 1.2 |
| | 13 | 97.3 | 1.1 |
| | 14 | 97.2 | 1.1 |
| | 15 | 97.1 | 1.1 |
| | 16 | 97.2 | 1.2 |
| | 17 | 97.2 | 1.0 |
| | 18 | 97.0 | 1.3 |
| Ex. 2-2 | 1 | 95.1 | 3.8 |
| | 2 | 85.7 | 13.2 |
| | 3 | 84.2 | 14.1 |
| | 4 | 78.0 | 20.0 |
| | 5 | 76.8 | 21.1 |
| | 6 | 76.0 | 21.7 |
| | 7 | 76.4 | 21.4 |
| | 8 | 73.4 | 24.6 |
| | 9 | 66.6 | 32.7 |
| | 10 | 64.9 | 32.7 |
| | 11 | 60.3 | 37.3 |
| | 12 | 54.7 | 43.1 |
| | 13 | 56.0 | 38.7 |
| | 14 | 54.2 | 44.8 |
| | 15 | 52.8 | 46.0 |
| | 16 | 50.6 | 47.9 |
| | 17 | 48.1 | 47.7 |
| | 18 | 41.5 | 53.0 |

As can be seen from Table 3 above, in Example 2-1, in which the catalyst bed had been fixed with the $CuZn/Al_2O_3$ catalyst and a solution in which the PHA pellets had been dissolved in an aprotic solvent was then fed and reacted, the yield of tetrahydrofuran was excellent. Specifically, the yield of tetrahydrofuran at the initial stage of the reaction was 98.6% by mole. Even after 18 hours, the yield of tetrahydrofuran was excellent at 97.0% by mole. In addition, the rate of decrease in the yield of tetrahydrofuran per hour was about 0.089% by mole, indicating stable activity.

In addition, in Example 2-2, in which the catalyst bed had been fixed with the $Cu/Al_2O_3$ catalyst and a solution in which the PHA pellets had been dissolved in an aprotic solvent was then fed and reacted, the rate of decrease in the yield of tetrahydrofuran with time tends to deteriorate as compared with Example 2-1 whereas the yield of tetrahydrofuran at the initial stage of the reaction was excellent at 95.1% by mole.

The invention claimed is:

1. A process for preparing tetrahydrofuran, gamma-butyrolactone, or 1,4-butanediol, which comprises subjecting a polyhydroxyalkanoate (PHA) to a hydrogenation reaction using a copper-based catalyst in an aprotic solvent.

2. The process for preparing tetrahydrofuran, gamma-butyrolactone, or 1,4-butanediol of claim 1, wherein the hydrogenation reaction is carried out at a temperature of 50° C. to 500° C. and a pressure of 1 bar to 100 bar.

3. The process for preparing tetrahydrofuran, gamma-butyrolactone, or 1,4-butanediol of claim 1, wherein hydrogen gas is injected in the hydrogenation reaction step, and the hydrogen gas is injected in a mole number of 1 time to 500 times the number of moles of the polyhydroxyalkanoate (PHA) monomer.

4. The process for preparing tetrahydrofuran, gamma-butyrolactone, or 1,4-butanediol of claim 1, which comprises mixing the polyhydroxyalkanoate (PHA) and the copper-based catalyst with the aprotic solvent; and subjecting the mixture to a hydrogenation reaction.

5. The process for preparing tetrahydrofuran, gamma-butyrolactone, or 1,4-butanediol of claim 4, which comprises, prior to the hydrogenation reaction step, removing oxygen in the reactor; and adjusting the internal pressure of the reactor to 1 bar to 100 bar by injecting hydrogen gas.

6. The process for preparing tetrahydrofuran, gamma-butyrolactone, or 1,4-butanediol of claim 4, wherein the weight ratio of the polyhydroxyalkanoate (PHA) to the copper-based catalyst is 1:0.01 to 5.

7. The process for preparing tetrahydrofuran, gamma-butyrolactone, or 1,4-butanediol of claim 4, wherein the hydrogenation reaction is carried out at a stirring speed of 200 rpm to 2,000 rpm for 1 hour to 10 hours.

8. The process for preparing tetrahydrofuran, gamma-butyrolactone, or 1,4-butanediol of claim 1, which comprises dissolving the polyhydroxyalkanoate (PHA) in the aprotic solvent; and passing the dissolved polyhydroxyalkanoate (PHA) through a catalyst bed comprising the copper-based catalyst to subject it to a hydrogenation reaction.

9. The process for preparing tetrahydrofuran, gamma-butyrolactone, or 1,4-butanediol of claim 8, wherein the weight hourly space velocity (WHSV) of the copper-based catalyst relative to the polyhydroxyalkanoate (PHA) is 0.1 $h^{-1}$ to 10 $h^{-1}$.

10. The process for preparing tetrahydrofuran, gamma-butyrolactone, or 1,4-butanediol of claim 1, wherein the copper-based catalyst is supported on a support, the support comprises at least one selected from the group consisting of carbon, zeolite, $Al_2O_3$, $SiO_2$, $TiO_2$, $ZrO_2$, MgO, and $Cr_2O_3$, the copper-based catalyst is a copper catalyst or a copper-metal composite catalyst, and the copper-metal composite catalyst comprises copper-metal complex which comprises at least one metal selected from the group consisting of Mn, Zn, Mg, Co, Ni, Cr, and Fe, other than copper.

11. The process for preparing tetrahydrofuran, gamma-butyrolactone, or 1,4-butanediol of claim 10, wherein the support is $Al_2O_3$, $SiO_2$, $TiO_2$, or $ZrO_2$, and the copper-based catalyst is a Cu catalyst, a Cu—Mn catalyst, a Cu—Zn catalyst, or a Cu—Mg catalyst.

12. The process for preparing tetrahydrofuran, gamma-butyrolactone, or 1,4-butanediol of claim 10, wherein the content of copper or copper-metal complex in the copper-based catalyst supported on the support is 0.1% by weight to 85% by weight based on the total weight of the support.

13. The process for preparing tetrahydrofuran, gamma-butyrolactone, or 1,4-butanediol of claim 1, wherein the aprotic solvent comprises at least one selected from the group consisting of acetone, dioxane, methyl acetate, ethyl acetate, N,N-dimethylformamide, N,N-dimethylacetamide, N-methylpyrrolidone, acetonitrile, propionitrile, butyronitrile, benzonitrile, acrylonitrile, dimethylsulfoxide, dichloromethane, dimethylpropylene urea, and hexamethylphosphate triamide.

14. The process for preparing tetrahydrofuran, gamma-butyrolactone, or 1,4-butanediol of claim 1, wherein the yield of tetrahydrofuran, gamma-butyrolactone, or 1,4-butanediol exceeds 65% by mole.

15. The process for preparing tetrahydrofuran, gamma-butyrolactone, or 1,4-butanediol of claim 1, which further comprises, prior to the hydrogenation reaction, pretreating the polyhydroxyalkanoate (PHA), wherein the pretreatment step comprises purifying the polyhydroxyalkanoate (PHA) using a solvent extraction method.

16. The process for preparing tetrahydrofuran, gamma-butyrolactone, or 1,4-butanediol of claim 1, which further comprises, after the hydrogenation reaction, treating the reaction product with one or more steps selected from the group consisting of a distillation step, an ion exchange step, a solvent extraction step, and an adsorption step.

17. The process for preparing tetrahydrofuran, gamma-butyrolactone, or 1,4-butanediol of claim 1, wherein the polyhydroxyalkanoate (PHA) comprises a 4-hydroxybutyrate (4-HB) repeat unit in an amount of 0.1% by weight to 100% by weight.

18. The process for preparing tetrahydrofuran, gamma-butyrolactone, or 1,4-butanediol of claim 1, wherein the polyhydroxyalkanoate (PHA) has an average particle size of 0.5 μm and 5 μm and a polydispersity index (PDI) of less than 2.5.

* * * * *